(12) United States Patent
Anderson et al.

(10) Patent No.: US 10,028,661 B2
(45) Date of Patent: Jul. 24, 2018

(54) BUFFERED BODY RETURN RECEIVER

(71) Applicant: MASSACHUSETTS INSTITUTE OF TECHNOLOGY, Cambridge, MA (US)

(72) Inventors: Grant S. Anderson, Salt Lake City, UT (US); Charles G. Sodini, Belmont, MA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 838 days.

(21) Appl. No.: 14/180,958

(22) Filed: Feb. 14, 2014

(65) Prior Publication Data

US 2015/0230707 A1      Aug. 20, 2015

(51) Int. Cl.
| | |
|---|---|
| *A61B 5/08* | (2006.01) |
| *A61B 5/00* | (2006.01) |
| *A61B 5/0402* | (2006.01) |
| *A61B 5/0476* | (2006.01) |
| *A61B 5/01* | (2006.01) |
| *A61B 5/145* | (2006.01) |

(Continued)

(52) U.S. Cl.
CPC .............. *A61B 5/0028* (2013.01); *A61B 5/01* (2013.01); *A61B 5/0402* (2013.01); *A61B 5/04004* (2013.01); *A61B 5/0428* (2013.01); *A61B 5/0476* (2013.01); *A61B 5/14542* (2013.01); *A61B 5/683* (2013.01); *A61B 5/6898* (2013.01); *A61B 5/7225* (2013.01)

(58) Field of Classification Search
USPC ................ 600/364, 300, 393, 509, 544, 549
See application file for complete search history.

(56) References Cited

U.S. PATENT DOCUMENTS

| | | | | |
|---|---|---|---|---|
| 6,211,799 B1 * | 4/2001 | Post | ..................... | A61B 5/0028 340/10.51 |
| 7,187,968 B2 * | 3/2007 | Wolf | ....................... | A61N 1/08 600/544 |

(Continued)

OTHER PUBLICATIONS

T. G. Zimmerman, "Personal Area Networks (PAN): Near-field intrabody communication," Master's thesis, Massachusetts Institute of Technology, Cambridge, 1995 (Zimmerman).*

(Continued)

*Primary Examiner* — Christian Jang
*Assistant Examiner* — Mitchell E Alter
(74) *Attorney, Agent, or Firm* — Talem IP Law, LLP (57) ABSTRACT

Buffered body return receiver configurations are described. An amplifier for a receiver can be connected to two electrodes such that one of the two electrodes is connected to a non-inverting input of the amplifier and a second of the two electrodes is a driven node by being connected to both the inverting input of the amplifier and the output of the amplifier. The amplifier may be connected as a fully differential amplifier, a single-ended differential amplifier, a buffer, or an amplifier with a gain greater than 1, while still enabling improved channel gains with reduced power consumption at the transmitter from the signal source. The buffered body return receiver is suitable for scenarios in which a signal source is electrically independent of the power supply of the receiver's amplifier.

20 Claims, 8 Drawing Sheets

(51) Int. Cl.
*A61B 5/04* (2006.01)
*A61B 5/0428* (2006.01)

(56) References Cited

U.S. PATENT DOCUMENTS

| | | | | |
|---|---|---|---|---|
| 8,639,329 B2* | 1/2014 | Brown | ............... | G01N 33/4836 435/283.1 |
| 2005/0113703 A1* | 5/2005 | Farringdon | ........... | A61B 5/0428 600/509 |
| 2006/0116599 A1* | 6/2006 | Davis | ................... | A61B 5/0536 600/547 |
| 2007/0078324 A1* | 4/2007 | Wijisiriwardana | | A41D 13/1281 600/386 |
| 2010/0315206 A1* | 12/2010 | Schenk | ................ | H04B 13/005 340/286.01 |
| 2013/0258319 A1* | 10/2013 | Schleicher | ............. | G01N 27/07 356/72 |

OTHER PUBLICATIONS

Wegmuller, M. S., et al., "Intra-body communication for biomedical sensor networks," Ph.D. dissertation, ETH Zurich, Ramistrasse 101, 8006 Zurich, Switzerland, Jul. 2007 (Wegmuller).*

Nagel, Joachim H. "Biopotential amplifiers." Bronzino JD: Biomedical engineering hand book, 2nd edition, Springer-Verlag New York (2000): 70-1 (Nagel).*

Bae, J., et al., "A 0.24-nj/b wireless body-area-network transceiver with scalable double-fsk modulation," IEEE Journal of Solid-State Circuits, Jan. 2012, vol. 47, No. 1, pp. 310-322.

Cho, N., et al., "The human body characteristics as a signal transmission medium for intrabody communication," IEEE Transactions on Microwave Theory and Techniques, May 2007, vol. 55, No. 5, pp. 1080-1086.

Xu, R., et al., "Electric-field intrabody communication channel modeling with finite-element method," IEEE Transactions on Biomedical Engineering, Mar. 2011, vol. 58, No. 3, pp. 705-712.

Callejon, M. A., et al. "Distributed circuit modeling of galvanic and capacitive coupling form intrabody communication," IEEE Transactions on Biomedical Engineering, Nov. 2012, vol. 59, No. 11, pp. 3263-3269.

Wegmueller, M., et al., "Galvanical coupling for data transmission through the human body," in Instrumentation and Measurement Technology Conference, 2006. Proceedings of the IEEE IMTC 2006, pp. 1686-1689.

Wegmuller, M. S., et al., "Intra-body communication for biomedical sensor networks," Ph.D. dissertation, ETH Zurich, Ramistrasse 101, 8006 Zurich, Switzerland, Jul. 2007.

* cited by examiner

BUFFERED BODY RETURN RECEIVER

BACKGROUND

Body coupled communication (BCC) refers to signal transmissions over a channel that includes a body. BCC uses the human body as a transmission medium for electrical data signals and is one of the techniques used for communication in wireless body area networks (BANs). BANs can be formed from devices, including sensors, that are near (proximate) or in direct contact with a body. Thus, BANs may also be referred to as body sensor networks (BSNs).

In a common configuration for medical applications, low power sensors are located on or in the body to monitor one or more vital signs of a patient and the signals from these sensors are transmitted to a base station, which may also be located on or proximate the patient. BCC enables wireless communication between the sensors and the base station by using electric fields to propagate a signal to a receiver.

One of the driving forces behind wearable, implantable, and attachable device design is power consumption, partly due to the small form factors associated with such devices. The wireless transmitters used in transmitting the information off the body (or to other devices on the body) can be one of the largest consumers of power for these devices. Thus, for BCC and other wireless communication modalities, the power efficiency of transmitters must be weighed against the ability of a receiver to read the signal.

BRIEF SUMMARY

Receivers are described herein that implement a buffered body return and which enable improved transmitter power consumption. For a device where the signal source is electrically independent to the power supply of the receiver's amplifier (whether acting as an amplifier or a buffer), an active node formed by feedback of the amplifier of the receiver enables reduced input impedance and increased channel gain.

The receiver can include two electrodes for coupling to a communication channel such as a body coupled communication channel and an amplifier receiving input from the two electrodes. The amplifier may be connected to a power supply electrically independent from a signal source from which a propagating signal is transmitted. One of the two electrodes can be connected to a non-inverting input of the amplifier; and a second of the two electrodes can be connected to an inverting input of the amplifier and an output of the amplifier as a driven node. The amplifier may be connected as a fully differential amplifier, a single-ended differential amplifier, a buffer, or an amplifier with a gain greater than 1.

In some implementations, the buffered body return configuration for the receiver can be incorporated as part of a physiological signal monitoring system.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DISCLOSURE

Communication systems and signal receivers are described that enable low power transmission of signals. The communication systems may include body coupled communication (BCC) channels. A BCC transmitter can transmit to a receiver as described herein at lower power levels without adversely affecting the magnitude of the received signal. By transmitting at lower power levels, the transmitter can become more power efficient. Such power efficiency is useful for long term monitoring (e.g., physiological signal, vital sign monitoring as well as other sensor node functions).

The described receivers may be implemented for any amplifier application having a power source isolated from the signal source. That is, the receiver configurations described herein may be used any time the signal source is electrically independent from the power supply of the amplifier. While specific examples are described in the context of BCC, embodiments are not limited to BCC.

The current path in a BCC method can be through the body and the environment or predominantly through the body. Implementations of the subject receivers are suitable for capacitive coupling and galvanic coupling of the electrodes. For both approaches, the BCC transceiver nodes consist of a transmitter (TX) and a receiver (RX), together connected to a coupler. Each coupler is composed of two electrodes that can couple the transceiver to a body.

Figure 1:
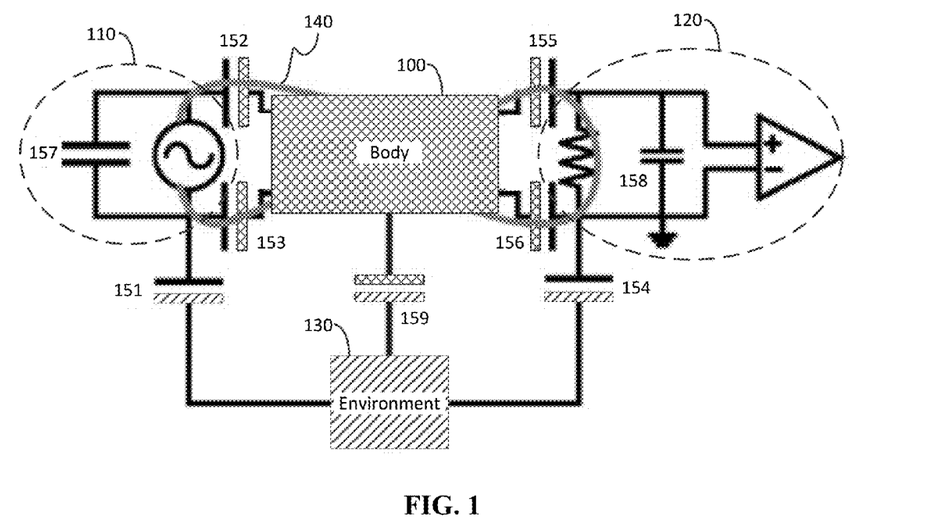
FIG. 1 illustrates a model for body coupled communication (BCC) with a BCC signal path.

FIG. 1 illustrates a model for BCC with a BCC signal path (indicated as line 140). A body 100, such as a human body, may form the channel for communication between a transmitter 110 and a receiver 120. Electrodes on the transmitter 110 and receiver 120 form capacitive links with the body 100 and the surrounding environment 130. For example, capacitive link 151 is formed between an electrode of the transmitter 110 and the environment 130, capacitive links 152 and 153 are respectively formed between the two electrodes of the transmitter 110 and the body 100, capacitive link 154 is formed between an electrode of the receiver 120 and the environment 130, and capacitive links 155 and 156 are respectively formed between the two electrodes of the receiver 120 and the body 100. A capacitive link 157 may form between the two electrodes of the transmitter and a capacitive link 158 may form between the two electrodes of the receiver 120. These two capacitive links 157 and 158 may be avoided by shielding the electrodes. A capacitive link 159 may also exist between the body 100 and the environment 130. Although elements 152, 153, 155, and 156 are shown as capacitive links, in certain implementations these elements may be in the form of resistive (or galvanic) links.

For some BCC signal paths, the current path is through both the body and the environment. This BCC signal path can be referred to as traditional BCC. In the traditional BCC arrangement, the capacitors 153 and 156 are parasitic capacitors and are minimized in order to direct the current to flow through the environment via capacitors 151 and 154. This can be accomplished by placing one electrode, from both the transmitter and the receiver, nearer to the body than the other electrode. For the BCC arrangement with a current path predominantly through the body (referred to herein as waveguide BCC), both electrodes of the transmitter and the receiver are attached to the body. Thus, the capacitive links 153 and 156 are part of the desired current path (and not parasitic). Based on these models, to receive the maximum amount of current from the transmitter to the receiver, the capacitors 153 and 156 are designed to have impedances as large as possible for the traditional BCC and are designed to have impedances as small as possible for the waveguide BCC.

Because the main current path for the waveguide BCC is through the body, the capacitive links to the environment (151, 154, 159) can be removed when modeling BCC.

Figure 2A:
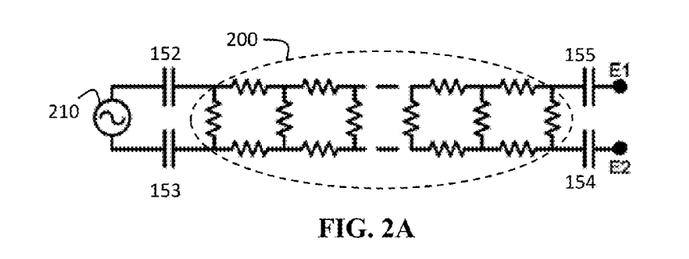
FIG. 2A illustrates a circuit model for the body in BCC.
Figure 2B:
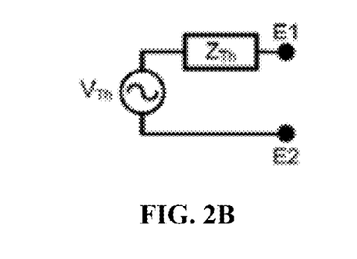
FIG. 2B illustrates an equivalent circuit model for the body in BCC.

FIG. 2A illustrates a circuit model for the body in BCC and FIG. 2B illustrates an equivalent circuit model for the body in BCC. Referring to FIG. 2A, the body may be modeled as a spread resistance 200 from the transmitter 210 to the receiver (not shown) that would be connected at electrodes E1 and E2.

As illustrated in FIG. 2B, the body and transmitter may be modeled as a Thevanin equivalent circuit with an equivalent voltage source Vth in series with an impedance Zth.

Because of the capacitive links, the DC Input bias point for the amplifier should be set to ensure that the amplifier's input does not cause the amplifier to saturate. For the largest signal to noise ratio (SNR), the bias impedance will match the channel. In practice, the BCC channel changes and can be difficult to match, resulting in the need for more power at the transmitter. Through a buffered body return configuration where one of the buffer (amplifier) inputs is driven by one of its outputs, a higher gain and even a higher SNR ratio may be available as compared to conventional receiver configurations in which the amplifier's input impedance and bias resistance is disposed between the electrodes (and the electrodes are connected as passive nodes).

Figure 3:
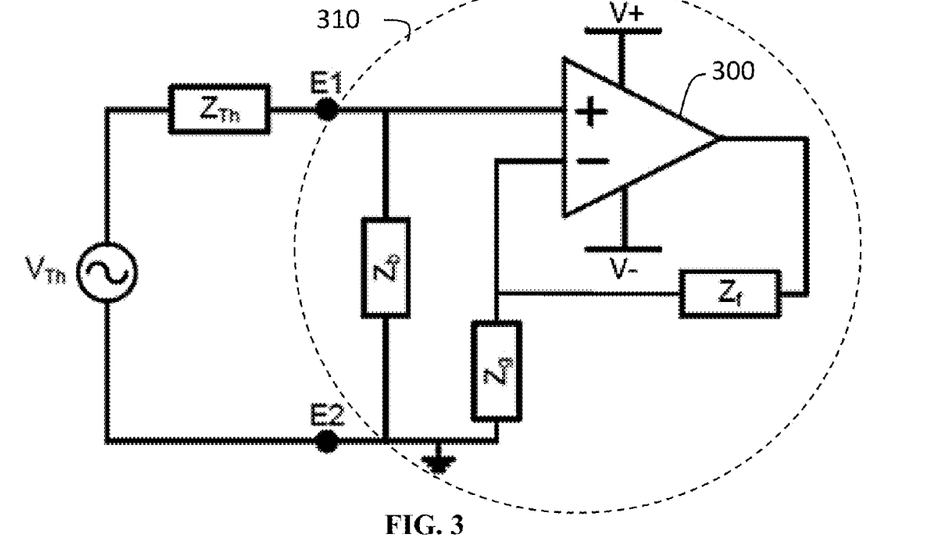
FIG. 3 illustrates an example configuration of a receiver for BCC having a traditional architecture.

FIG. 3 illustrates an example configuration of a receiver for BCC having a traditional architecture. As shown in FIG. 3, an amplifier 300 in a conventional BCC receiver configuration 310 is coupled to the ground, as a bias, and to electrodes E1 and E2. In this configuration, the ground is the mid-rail voltage of the receiver amplifier 300. In addition to the input resistance to the amplifier 300, impedance Zb includes a resistance to set the bias of the receiver amplifier 300. Based on the model shown in FIG. 2A, for this traditional method, the BCC channel can be characterized as a first high-pass filter formed by the capacitive links 152 and 153 from the transmitter 210 and the spread resistance 200 of the body and a second high-pass filter formed by the capacitive links 154 and 155 and the impedance Zb. The gain of the traditional configuration 310 can be given by:

$$\text{Gain} = \frac{Z_b}{Z_{Th} + Z_b}\left(1 + \frac{Z_f}{Z_g}\right) = \frac{Z_b}{Z_{Th} + Z_b}A,$$

where A is the gain of the amplifier 300.

Figure 4:
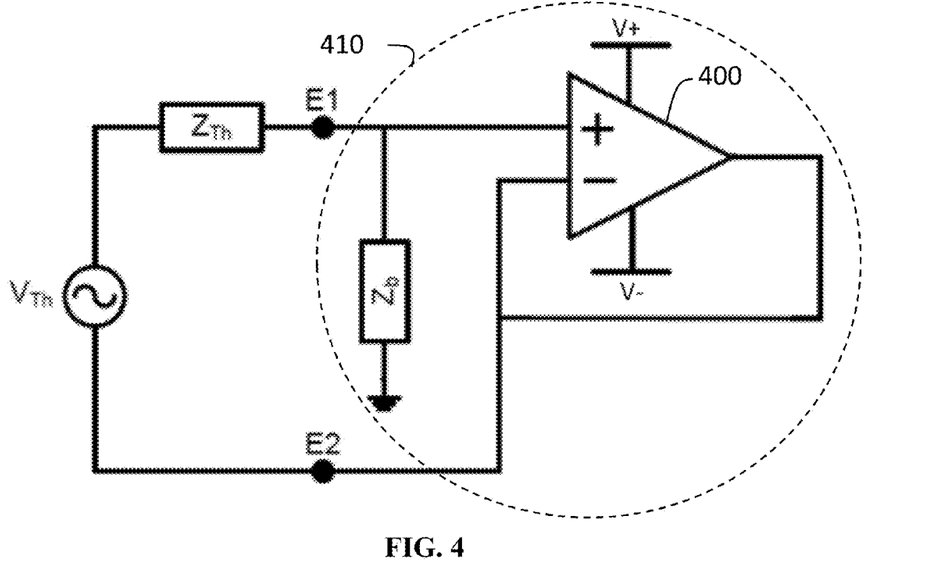
FIG. 4 illustrates an example configuration for a receiver for buffered body return that may be used in body coupled communication.

FIG. 4 illustrates an example configuration for a receiver for buffered body return that may be used in body coupled communication. As shown in FIG. 4, an amplifier 400 in a buffered body return configuration 410 can also be coupled to the ground (as a bias), and to electrodes E1 and E2. In addition, impedance Zb can include the input impedance of the amplifier 400 and a resistance to set the bias of the receiver amplifier 400. Previously, as described with respect to the traditional method, a first electrode is provided at the input to the amplifier/buffer and a second electrode is connected to a static voltage. Now, for the buffered body return configuration 410, the first electrode is still provided at the input to the amplifier/buffer 400, but the second electrode is connected as a feedback buffered input signal to the BCC channel. Thus, as illustrated in FIG. 4, the feedback causes the channel to see a short and the gain for the receiver configuration 410 (from the output of the transmitter to the output of the buffer/amplifier 400) can be given by:

$$\text{Gain} = \frac{Z_b}{Z_{th}}.$$

It should be understood that in some implementations of this or other configurations of receivers described herein, the bias voltage can be another voltage instead of ground or the mid-rail voltage.

Figure 5:
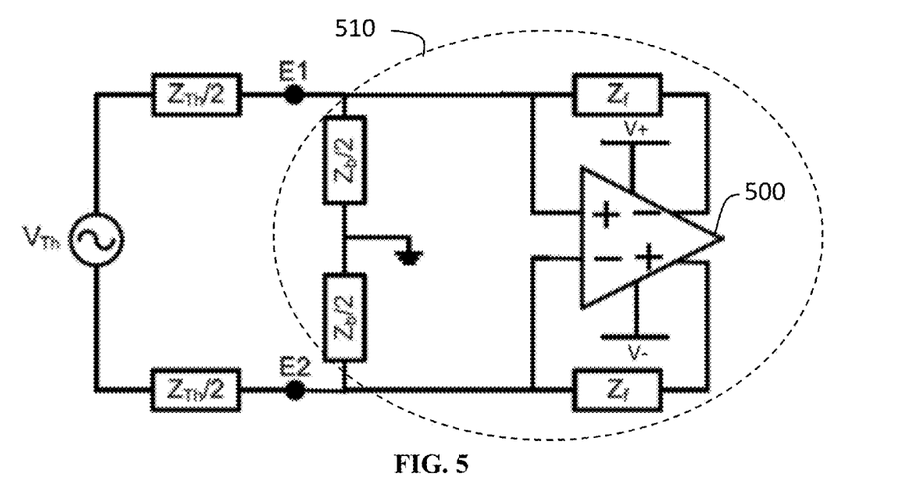
FIG. 5 illustrates an example configuration for a fully differential receiver for buffered body return that may be used in body coupled communication.

FIG. 5 illustrates an example configuration for a fully differential receiver for buffered body return that may be used in body coupled communication. As shown in FIG. 5, a differential amplifier 500 can be connected in a fully-differential buffered body return configuration 510. The ground is again the mid-rail voltage of the receiver and used to bias the amplifier in this example configuration. Similar to the configuration 410 shown in FIG. 4, the feedback from the amplifier 510 causes the channel to see a short. However, the impedance Zb no longer affects the gain of the amplifier 500. Instead, the bias impedance Zb can be used for when Zf (the feedback impedance) is large to decrease the time constant of setting DC value. The gain of the differential amplifier receiver configuration 510 (from the output of the transmitter to the output of the amplifier 500) can be given by:

$$\text{Gain} = \frac{2Z_f}{Z_{th}}.$$

In the configuration shown in FIG. 5, the common-mode signals can be rejected at the electrode and common-mode feedback may be included in some implementations.

Figure 6:
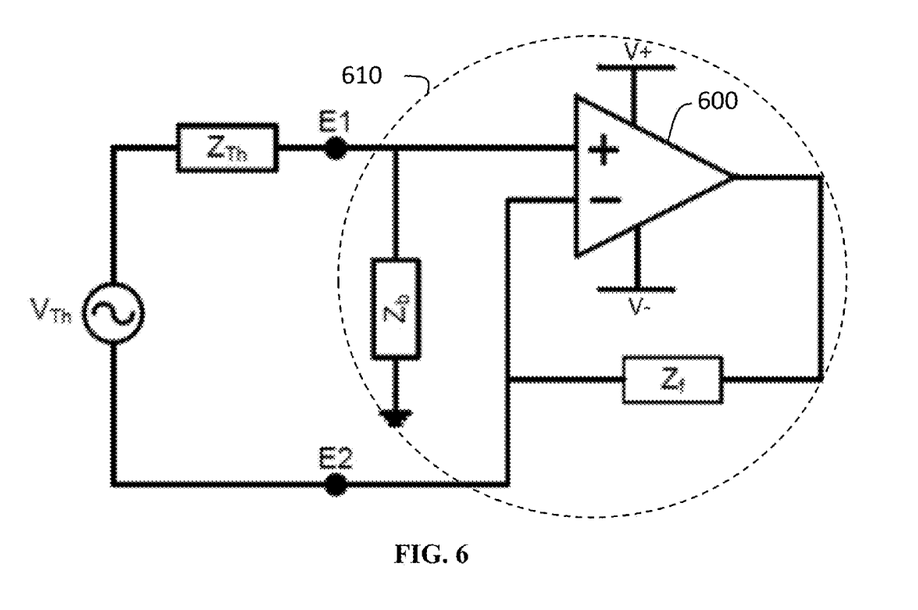
FIG. 6 illustrates an example configuration for a differential receiver for buffered body return that may be used in body coupled communication.

FIG. 6 illustrates an example configuration for a differential receiver for buffered body return that may be used in body coupled communication. As shown in FIG. 6, an amplifier 600 can be connected in a single-ended differential buffered body return configuration 610. Again, the ground is the mid-rail voltage of the receiver amplifier 600, and is used to bias the amplifier, and the feedback causes the channel to see a short. In this configuration, the common-mode signals can be rejected at the electrode if Zb=Zf and common-mode feedback can easily be omitted. The gain of the receiver configuration 610 can be given by:

$$\text{Gain} = \frac{Z_f + Z_b}{Z_{Th}}$$

(and Zb=Zf for high common-mode rejection ratio).

As illustrated in the example configurations of FIGS. 4, 5, and 6, the buffered body return connects one of the receiver's electrodes to the input of an amplifier and the other to the amplifier's output. The active output can be amplified, but many applications can be designed for a gain of 1 (and thus the amplifier may be referred to as a buffer). In the buffered case, the feedback creates a "virtual short" as seen by the channel.

Figure 7:
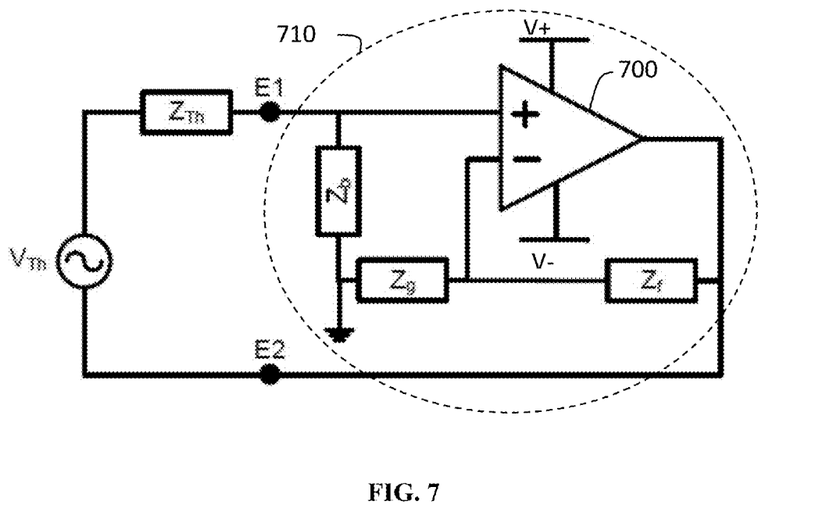
FIG. 7 illustrates an example configuration of a receiver with for an amplified buffered body return.

FIG. 7 illustrates an example configuration of a receiver for an amplified buffered body return. In the general case of an amplified buffered body return, the ground is again the mid-rail voltage of the receiver amplifier 700, however, a gain impedance Zg can be included to increase the gain since the amplifier 700 gain $$A = 1 + \frac{Z_f}{Z_g}.$$

Precisely choosing A can yield a high overall gain as can be seen by the gain of the amplified receiver configuration 710 given by:

$$\text{Gain} = \frac{1}{\frac{Z_{Th}}{Z_b} + 1 - A}.$$

Precise selection of A can, in some cases, be a challenge due to the dependency on Zth and the risk of positive feedback direct to the input. However, even without A>1, more gain is possible through the buffered body return configuration as compared to the traditional method because gain can be increased for the buffered body return when Zth is small compared to Zb, which is opposite the traditional method.

As an illustration of the body buffered return configuration providing a higher gain than the traditional method, the Gain ($G_{BBR}$) of the configuration shown in FIG. 4 can be compared to the Gain ($G_{T-BCC}$) of the configuration shown in FIG. 3. In particular, $G_{BBR} \geq G_{T-BCC}$ where Zb is larger than Zth because $$\frac{Z_b}{Z_{Th}} \geq \frac{Z_b}{Z_{Th} + Z_b} A,$$

which gives $Z_b \geq Z_{th}(A-1)$.

The buffered body return can potentially also show a higher signal to interferer ratio. For example, the signal (S) and interferer (I) for the buffered body return configuration 410 shown in FIG. 4 can be given as $$S = \frac{Z_b}{Z_S} \text{ and } I = \frac{Z_b}{Z_I},$$

respectively; whereas the signal and interferer for the traditional method can be given as $$S = \frac{Z_b}{Z_b + Z_S} A \text{ and } S = \frac{Z_b}{Z_b + Z_I} A,$$

respectively. Thus, it can be noted that $$\frac{Z_I}{Z_S} \geq \frac{Z_I + Z_b}{Z_S + Z_b}$$

since for $Z_I \gg Z_b$, $$1 \geq \frac{Z_S}{Z_S + Z_b}.$$

Figure 8:
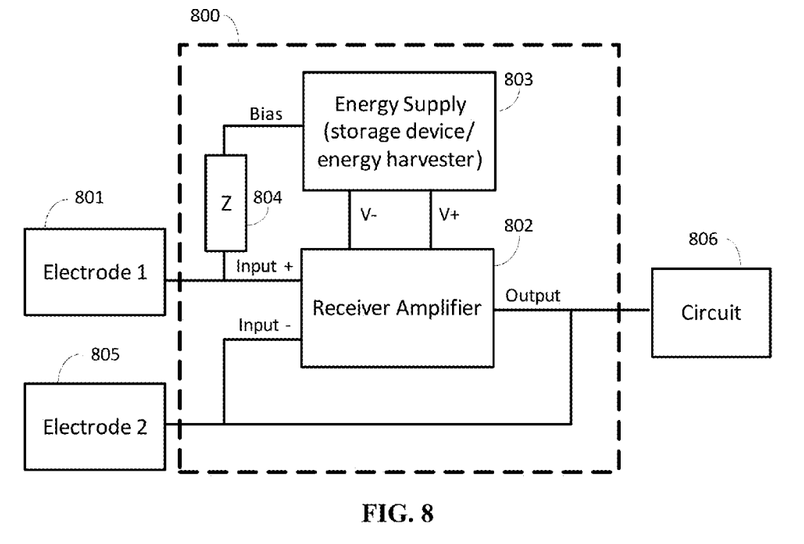
FIG. 8 illustrates a diagram of a buffered body return receiver chip.

FIG. 8 illustrates a diagram of a buffered body return receiver chip. Referring to FIG. 8, a chip with a buffered body return receiver 800 can include a first electrode 801 connected to a receiver amplifier 802 that is powered by an energy supply 803. The receiver amplifier 802 may be any suitable amplifier such as a discrete op amp or an integrated amplifier/processor circuit on a CMOS (complementary metal oxide semiconductor) or other technology IC (integrated circuit) chip. The energy supply 803 may be a storage device such as a capacitor, battery and/or include an energy harvesting device. The energy supply 803 is electrically independent from the signal source to which the receiver is receiving a signal. Bias impedance 804 can be included between the first electrode 801 and a reference ("Bias"). A second electrode 805 is connected to the receiver 802 both at an inverting input and at the output, resulting in the second electrode 805 being driven by the amplifier 802. Additional circuitry 806 can be included on the chip to process the signal obtained from the receiver 802. The additional circuitry 806 can include an analog to digital converter, digital signal processing, analog processing, a transmitter, a memory device, or other such circuits or processors. The additional circuitry 806 may be on-chip or part of the same package as the buffered body return receiver 800.

Implementations may include lifestyle and healthcare applications. A lifestyle application includes wearable technology and computing solutions in which multiple devices may wirelessly communicate with each other. Healthcare applications include patient monitoring both inside and outside a medical environment; and can involve monitoring and/or measuring electrocardiogram (ECC) signals, electroencephalogram (EEG) signals, body temperature, and blood oxygenation as just a few examples.

The receivers described herein may be incorporated into a physiological signal monitoring system. The physiological signal may include one or more vital sign measures, such as heart beat, breathing rate, temperature, and blood pressure. The physiological signal monitoring system may include sensor node packages for providing the signal source that is received by the receivers. A storage device may be on chip or in a same package as the receiver chip to store data corresponding to received signals. As an addition or an alternative, a wireless transmitter can be connected to the output of the amplifier for transmitting received signals to a computing device or storage device that is located off-body or at another location on or about a person's body.

The buffered body return receiver can be suitable for receiving EEG signals, for example where an electrode is implanted between the skin of the skin and the person's skull, and the first and second electrode of the buffered body return receiver are attached to the scalp or another region of the person's body. As an alternative to direct attachment, the buffered body return receiver can be an attachment to or part of a mobile phone (cell phone, smart phone), phablet, or other mobile computing device; and the electrodes can be exposed in a manner that the phone (or other mobile computing device) can be touched to the skin to connect to the body channel via the exposed electrodes of the mobile computing device. As yet another implementation, the receiver and electrodes can be part of or attached to a wearable mobile computing device such as a watch-based computing device or a glasses-based computing device.

Figure 9:
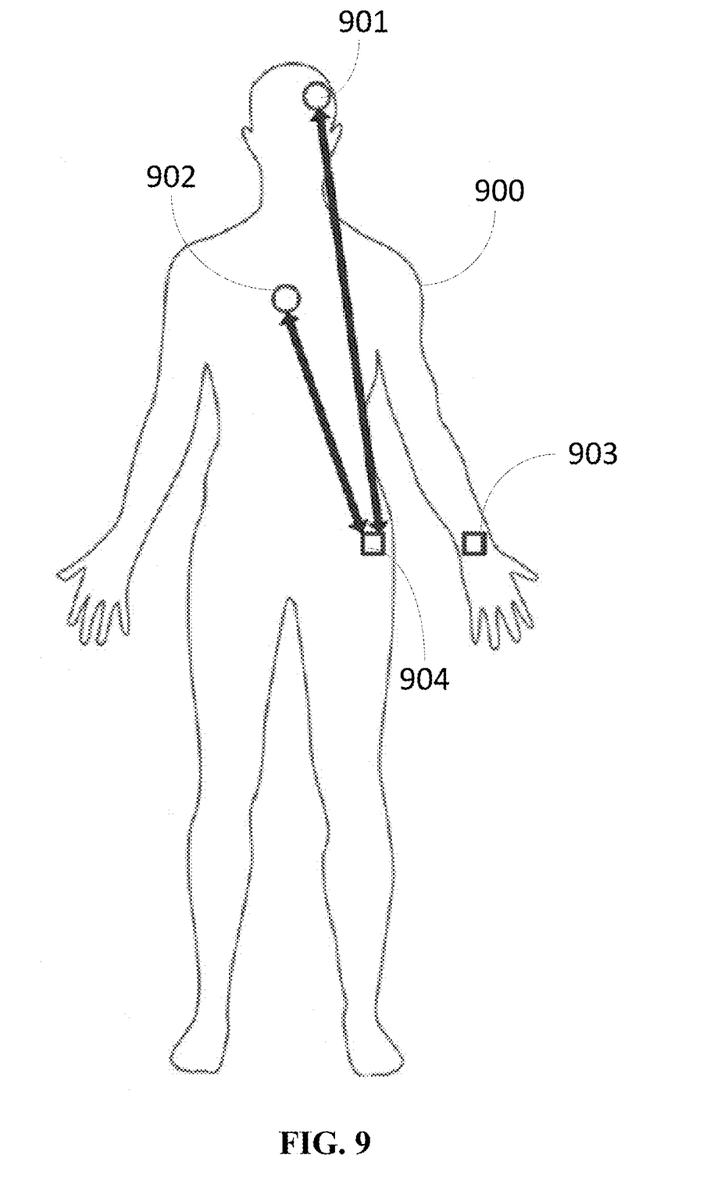
FIG. 9 illustrates an example scenario of a body area network in which a buffered body return receiver may be used.

FIG. 9 illustrates an example scenario of a body area network in which a buffered body return receiver may be used. Referring to FIG. 9, one or more sensors may be implanted or otherwise attached to a body 900 of a person. The sensors can provide the signal sources received by the buffered body return receiver. One sensor 901 may detect brain signals and another sensor 902 may detect heart or lung related signals. A device, such as a computer watch 903, may be worn by the person to receive signals from the sensors 901 and 902. Alternatively, a receiving device 904 may be worn as a patch on the person's thigh or provided as part of a device that the person may keep in a pocket. For one scenario, the patch can be an electrode patch for releasably attaching the first electrode and the second electrode to a body. In some cases, multiple receivers may be worn. For both cases, two electrodes can be provided as part of the device in a manner that couples the electrodes to the body 900.

As a non-healthcare related example, the buffered body return receiver can also be suitable for detecting signals from a piezoelectric transducer that may not be directly accessible. For cases where the signal source is a piezo transducer, it is possible to amplify the signal without having to tie the ground of the power supply to the node of the piezo transducer. Instead, it is possible to connect to the output of the buffer instead.

Example—Prototype

To illustrate the effectiveness of the buffered body return, a simplified BCC model and buffered body return receiver were simulated and a prototype was generated. First, the receiver was optimized for BCC to increase the gain in the channel, where the channel is defined as the transfer function from the output of the transmitter, to the input of the receiver (and includes capacitive links as part of the channel). As described with respect to FIG. 2A, the channel can be a combination of two high-pass filters.

As the input resistance of the receiver increases, one of the high-pass filter's pass band will increase, and its corner frequency will decrease. Both effects provide higher gain in the BCC channel over the frequency band of interest; thus, increasing the input resistance can increase the gain. However, as the input resistance increases it is easier for any stray signals to couple into the input of the receiver, including the receiver's own amplified signal, causing positive feedback and limiting how large the input resistance can be.

In the traditional method, one of the receiver's electrodes is connected to the input of the receiver's amplifier, with the other electrode connected to a bias (e.g., ground) as shown in FIG. 3. In this configuration, the current flowing through the receiver's input resistance creates a potential difference between nodes E1 and E2, which means the resistance directly loads the transmitter. Because the input impedance (Zb) loads the transmitter, as the resistivity of Zb increases the signal current will decrease. However, the decrease in current is not proportional to the increase in resistance. Thus the voltage drop between E1 and E2 will still increase.

If the electrodes are connected to the receiver as shown in FIG. 4 (as well as FIGS. 5 and 6), then the buffer will ensure that nodes E1 and E2 are at the same potential, which means the input resistance no longer loads the transmitter. This also means the same current can flow through the input resistor regardless of its size. Because the current stays the same regardless of resistor size, then the larger the resistor (or bias impedance Zb) the larger the voltage drop across this impedance. Because the voltage across the input impedance increases, it is possible to increase gain in the channel without an increase of output-voltage from the transmitter. Thus, by returning current back through the body, the gain in the BCC channel increases.

Figure 10:
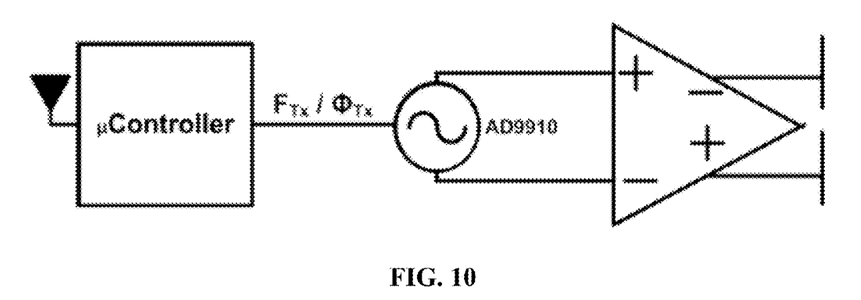
FIG. 10 illustrates a functional schematic of the transmitter.
Figure 11:
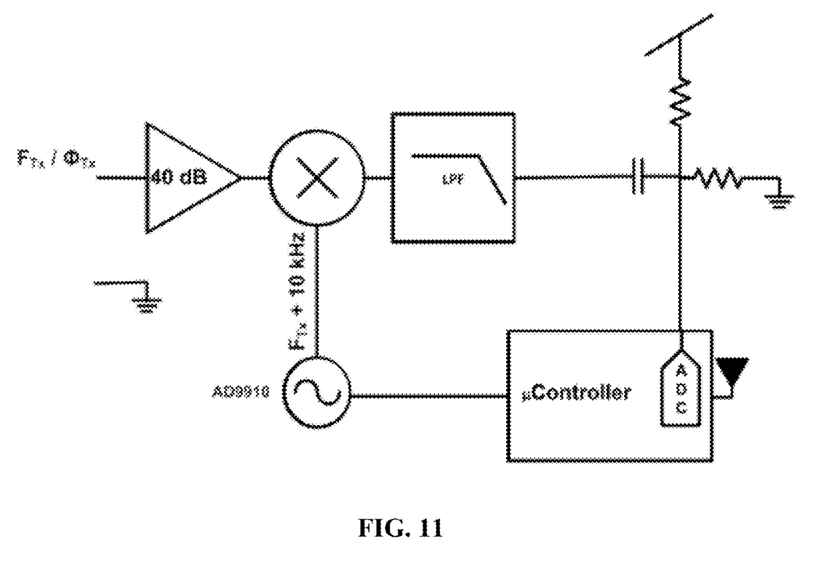
FIG. 11 illustrates a functional schematic of the receiver.

To make accurate measurements of the BCC channel, a discrete transmitter and receiver were made with commercially available parts. The nodes were powered by battery and are not connected in any way, other than through the BCC channel. The transmitter design is shown in FIG. 10 and the receiver design is shown in FIG. 11. To facilitate measuring the channel gain for the buffered body return receiver, one of the receiver's electrodes can either be connected to the receiver's ground, or the output of a unity gain buffer.

The frequency response of the BCC channel was measured by controlling the transmitter, using radio, to output a sine wave with a frequency of $F_{Tx}$. The receiver was controlled by radio to multiply the received signal with a sine wave of frequency $F_{Tx}+10$ kHz. The output of the multiplier had frequency components at 10 kHz and $2F_{Tx}+10$ kHz. After low-pass filtering, the 10 kHz output of the receiver was digitized and sent off the node using radio. Because the amplitude of the 10 kHz signal is proportional to the input amplitude of $F_{Tx}$, the 10 kHz signal could be input-referred to the amplitude of the received signal, which is the output of the channel. The amplitude of the channel's input was captured using a high impedance probe and oscilloscope. The magnitude of the channel's frequency response was then calculated as the amplitude of both the input and output of the channel were known.

Figure 12:
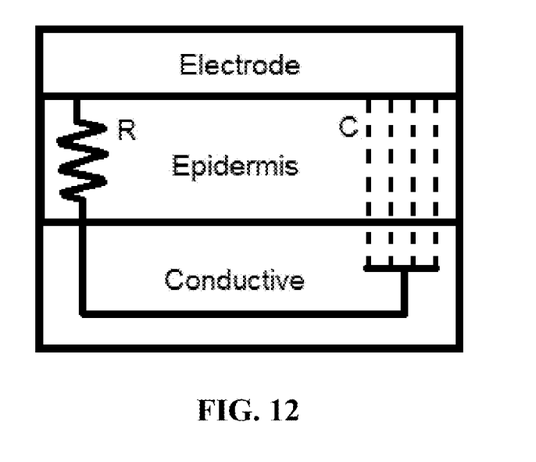
FIG. 12 illustrates a representation of a BCC link.
Figure 13:
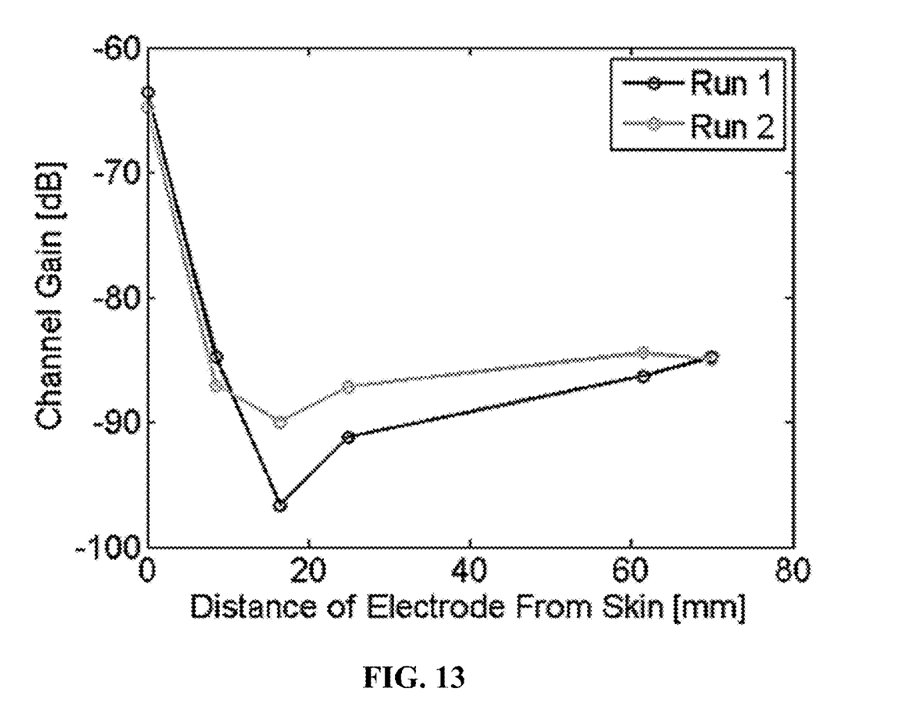
FIG. 13 shows a plot of distance of the second electrode from skin versus channel gain.
Figure 14:
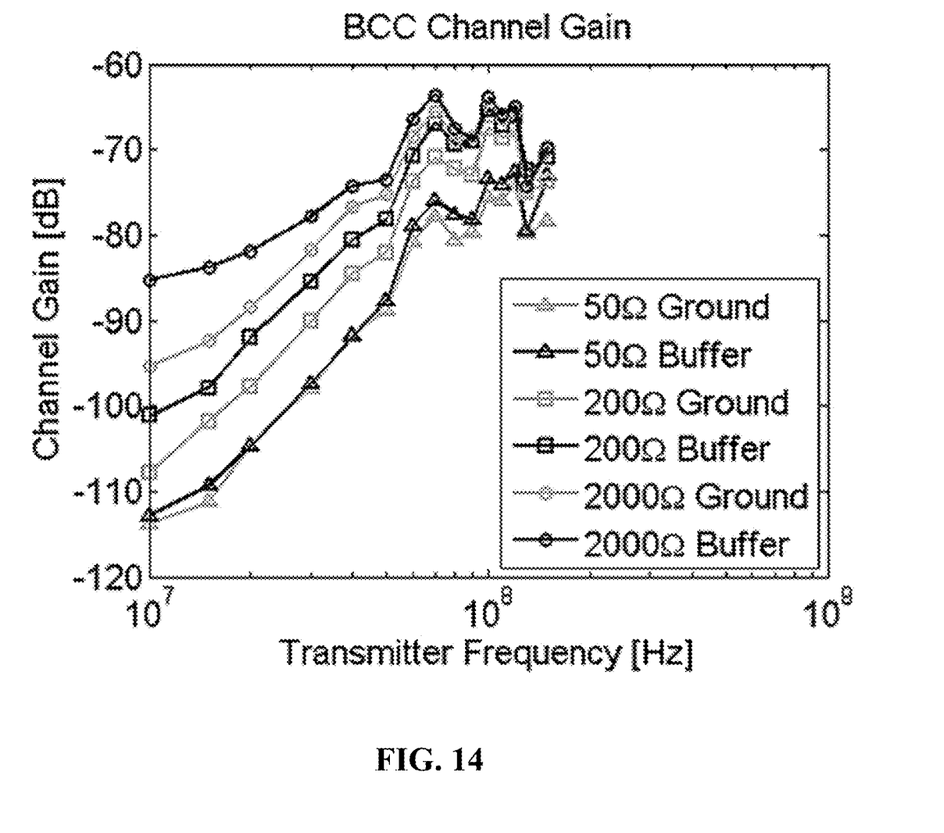
FIG. 14 shows a plot of the magnitude frequency response for the BCC channel.

The following measurements were made using the transmitter and receiver detailed above. By placing the electrodes on the skin a galvanic and capacitive connection is made as modeled in FIG. 12. Referring to FIG. 12, while there is a resistive element to the BCC link, it is dominated by the capacitance at frequencies 10 MHz and above. The resistance through the epidermis to the conductive tissue was found to be 1.5 MΩ, while the capacitance to the conductive tissue was found to be 10 pF. The total impedance of this connection at frequencies of 10 MHz and above is dominated by the capacitance.

As discussed with respect to FIG. 1, the capacitors 153 and 156 are designed to have impedances as small as possible for the waveguide BCC. As the impedance of 156 increases, the gain of the channel decreases. For example, referring to FIG. 15, as the distance between the second electrode and the body increases, the impedance of the second electrode increases, and the gain in the channel decreases.

For this experiment the transmitter was attached to the deltoid of the left arm, while the receiver was attached to the wrist of the left arm. The frequency of the signal being sent for the test was 60 MHz. Again with reference to FIG. 1, both electrodes on the transmitter 110 were fixed in position on the body 100 to keep capacitors 151, 152, 153, and 157 constant. One electrode on the receiver 120 was also fixed in position on the body to keep capacitor 155 constant. The distance between the body 100 and the receiver's other electrode, which forms capacitor 156, was varied using cardboard spacers. As the electrode was moved farther away from the body, the impedance of 156 increased and was correlated with a decrease in channel gain.

To measure the BCC channel gain, the transmitter was placed on the head with one electrode on the forehead and the other on the mastoid behind the ear. The receiver was placed on the waist with the electrodes attached near the belt line. The frequency was swept over the 10 MHz-150 MHz range. Three different resistance values were tested for the input resistance of the receiver: 50 Ω, 200Ω, and 2,000Ω. For each resistance the test was run twice. Once with the electrode making capacitor 156 connected to the receiver's mid-rail voltage, or "ground", and once with the electrode connected to the buffered output of the receiver's input, to test the effectiveness of the buffered body return. The results are shown in FIG. 16.

Restricting analysis to only the results for the ground return, with a 50 Ω input resistance there is about a 40 dB/dec increase in channel gain between 10 and 100 MHz due to the channel acting like two high-pass filters. An increase in the input resistance results in an increase in the flat-band gain. Also the slope decreases with the increase in resistance, which suggests that the corner frequency of one of the high-pass filters is moving to a lower frequency. Both effects are predicted by the model illustrated in FIGS. 2A and 2B.

When buffered body return is used, the same current will flow through the input resistance of the receiver regardless of its impedance. Thus, as the input resistance increases the gain in the channel should also increase by the same factor. In the test, it was expected that there would be a gain increase of 12 dB and 20 dB between the increase from 50Ω to 200Ω and 200Ω to 2,000Ω respectively. At lower frequencies the gain increase for the buffered body return between 50Ω and 200Ω was 12 dB. At higher frequencies the gain increase from the buffered body return decreases. The tapering effect found in the test may be a result of high frequency parasitics, and adverse high frequency effects of the amplifier.

Any reference in this specification to "one embodiment," "an embodiment," "example embodiment," "an implementation," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

We claim:

1. A buffered body return receiver, comprising:
   an amplifier connected to a power supply electrically independent from a signal source;
   a first electrode directly connected to a non-inverting input of the amplifier; and
   a second electrode connected to an inverting input of the amplifier and an output of the amplifier as a driven node, the second electrode appearing as a virtual short with respect to the first electrode.

2. The buffered body return receiver of claim 1, further comprising:
   a bias impedance connected between the first electrode and a bias voltage at a mid-point voltage level of the power supply.

3. The buffered body return receiver of claim 1, wherein the amplifier comprises a differential amplifier.

4. The buffered body return receiver of claim 3, further comprising:
   a first bias impedance connected between the first electrode and a node at a bias voltage;
   a second bias impedance connected between the second electrode and the node at the bias voltage;
   a first feedback impedance connected between the output of the amplifier and the non-inverting input of the amplifier; and
   a second feedback impedance connected between the output of the amplifier and the inverting input of the amplifier.

5. A buffered body return receiver, comprising:
   an amplifier connected to a power supply electrically independent from a signal source;
   a first electrode directly connected to a non-inverting input of the amplifier;
   a second electrode connected to an inverting input of the amplifier and directly connected to an output of the amplifier; a bias impedance connected between the first electrode and a node at a bias voltage;
   a feedback impedance connected between the output of the amplifier and the inverting input of the amplifier; and
   a gain impedance connected between the inverting input of the amplifier and the node at the bias voltage.

6. A physiological signal monitoring system, comprising:
   a power supply electrically independent from a signal source; and
   a buffered body return receiver comprising an amplifier connected to the power supply; a first electrode directly connected to a non-inverting input of the amplifier; and a second electrode connected to an inverting input of the amplifier and an output of the amplifier as a driven node, the second electrode appearing as a virtual short with respect to the first electrode, wherein the first electrode and the second electrode are configured for contact to a body.

7. The physiological signal monitoring system of claim 6, further comprising:
   a bias impedance connected between the first electrode and a bias voltage at a mid-point voltage level of the power supply.

8. The physiological signal monitoring system of claim 6, wherein the amplifier comprises a differential amplifier.

9. The physiological signal monitoring system of claim 8, further comprising:
a first bias impedance connected between the first electrode and a node at a bias voltage;
a second bias impedance connected between the second electrode and the node at the bias voltage;
a first feedback impedance connected between the output of the amplifier and the non-inverting input of the amplifier; and
a second feedback impedance connected between the output of the amplifier and the inverting input of the amplifier.

10. The physiological signal monitoring system of claim 6, further comprising:
a bias impedance connected between the first electrode and a node at a bias voltage; and
a feedback impedance connected between the output of the amplifier and the inverting input of the amplifier.

11. A physiological signal monitoring system, comprising:
a power supply electrically independent from a signal source;
a buffered body return receiver comprising an amplifier connected to the power supply;
a first electrode directly connected to a non-inverting input of the amplifier;
a second electrode connected to an inverting input of the amplifier and directly connected to an output of the amplifier;
a bias impedance connected between the first electrode and a node at a bias voltage;
a feedback impedance connected between the output of the amplifier and the inverting input of the amplifier; and
a gain impedance connected between the inverting input of the amplifier and the node at the bias voltage, wherein the first electrode and the second electrode are configured for contact to a body.

12. The physiological signal monitoring system of claim 6, further comprising:
a sensor node package for implantation in a body, the sensor node package comprising a sensor and a transceiver, the sensor providing the signal source.

13. The physiological signal monitoring system of claim 12, wherein the buffered body return receiver receives electrocardiogram signals, electroencephalogram signals, body temperature signals, or blood oxygenation signals from the transmitter.

14. The physiological signal monitoring system of claim 6, further comprising an electrode patch for releasably attaching the first electrode and the second electrode to a body.

15. The physiological signal monitoring system of claim 6, further comprising a storage device connected to the buffered body return receiver and storing data corresponding to received signals.

16. The physiological signal monitoring system of claim 6, further comprising a transmitter connected to the output of the amplifier for transmitting received signals.

17. The physiological signal monitoring system of claim 6, wherein the first electrode and the second electrode are disposed on an outer surface of a mobile computing device.

18. The physiological signal monitoring system of claim 17, wherein the mobile computing device comprises a wearable computing device.

19. The physiological signal monitoring system of claim 17, wherein the mobile computing device comprises a mobile phone or phablet.

20. The buffered body return receiver of claim 1, wherein the first electrode and the second electrode are configured for contact to a body.

* * * * *